US00PP28093P2

(12) United States Plant Patent
Wood

(10) Patent No.: US PP28,093 P2
(45) Date of Patent: Jun. 13, 2017

(54) ***CARYOPTERIS* 'SMNCVH'**

(50) Latin Name: *Caryopteris incana*
Varietal Denomination: SMNCVH

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 14/998,757

(22) Filed: Feb. 9, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

PLUTO Plant Variety Database Jan. 25, 2017. p. 1.*

* cited by examiner

*Primary Examiner* — Annette Para
(74) *Attorney, Agent, or Firm* — Cassandra Bright

(57) ABSTRACT

A new and distinct *Caryopteris* cultivar named 'SMNCVH' is disclosed, characterized by attractive yellow-green foliage improved hardiness and compact growth habit. The new variety is a *Caryopteris*, normally used for ornamental horticulture purposes.

3 Drawing Sheets

Latin name of the genus and species: *Caryopteris incana.*
Variety denomination: 'SMNCVH'.

BACKGROUND OF THE INVENTION

The new *Caryopteris* cultivar is a product of a planned breeding program conducted by the inventor, Timothy D. Wood, in Grand Haven, Mich. The objective of the breeding program was to produce new *Caryopteris* varieties for ornamental commercial applications. The open pollination resulting in this new variety was made during August of 2005.

The seed parent is the, commercial variety referred to as *Caryopteris* 'Jason' (Sunshine Blue) patent application pending. The pollen parent is unknown as it was an open pollination breeding program. The new variety was selected July of 2013 by the inventor in a group of seedlings resulting from the 2005 open pollination, in a seedling trial field in Grand Haven, Mich.

Asexual reproduction of the new cultivar was performed by softwood cuttings. This was first performed at Spring Meadow Nursery in Grand Haven, Mich. during July of 2013 and has shown that the unique features of this cultivar are stable and reproduced true to type in 4successive generations.

SUMMARY OF THE INVENTION

The cultivar 'SMNCVH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNCVH' These characteristics in combination distinguish 'SMNCVH' as a new and distinct *Caryopteris* cultivar:

1. Attractive yellow-green foliage.
2. Compact growth habit.
3. Improved hardiness Plants of the new cultivar 'SMNCVH' are similar to plants of the seed parent, *Caryopteris* 'Jason' in most horticultural characteristics, however, plants of the new cultivar 'SMNCVH' differ in the following;

1. Better winter cold hardiness
2. More compact in plant habit.

COMMERCIAL COMPARISON

Plants of the new cultivar 'SMNCVH' are comparable to the patented commercial variety *Caryopteris* 'Janice' U.S. Plant Pat. No. 22,160 (Lil Miss Sunshine). The two *Caryopteris* varieties are similar in most horticultural characteristics; however, the new variety 'SMNCVH' differs in the following:

1. Comparator is more compact in habit.
2. Yellow-green foliage. The comparator has yellow foliage.
3. Longed lived.

BRIEF DESCRIPTION OF THE PHOTOGRAPHS

The accompanying photograph in FIG. 1 illustrates in full color a typical mature plant of 'SMNCVH' grown outdoors in Grand Haven, Mich. Age of the plant photographed is approximately 2 years old from a rooted cutting.

Figure 1:
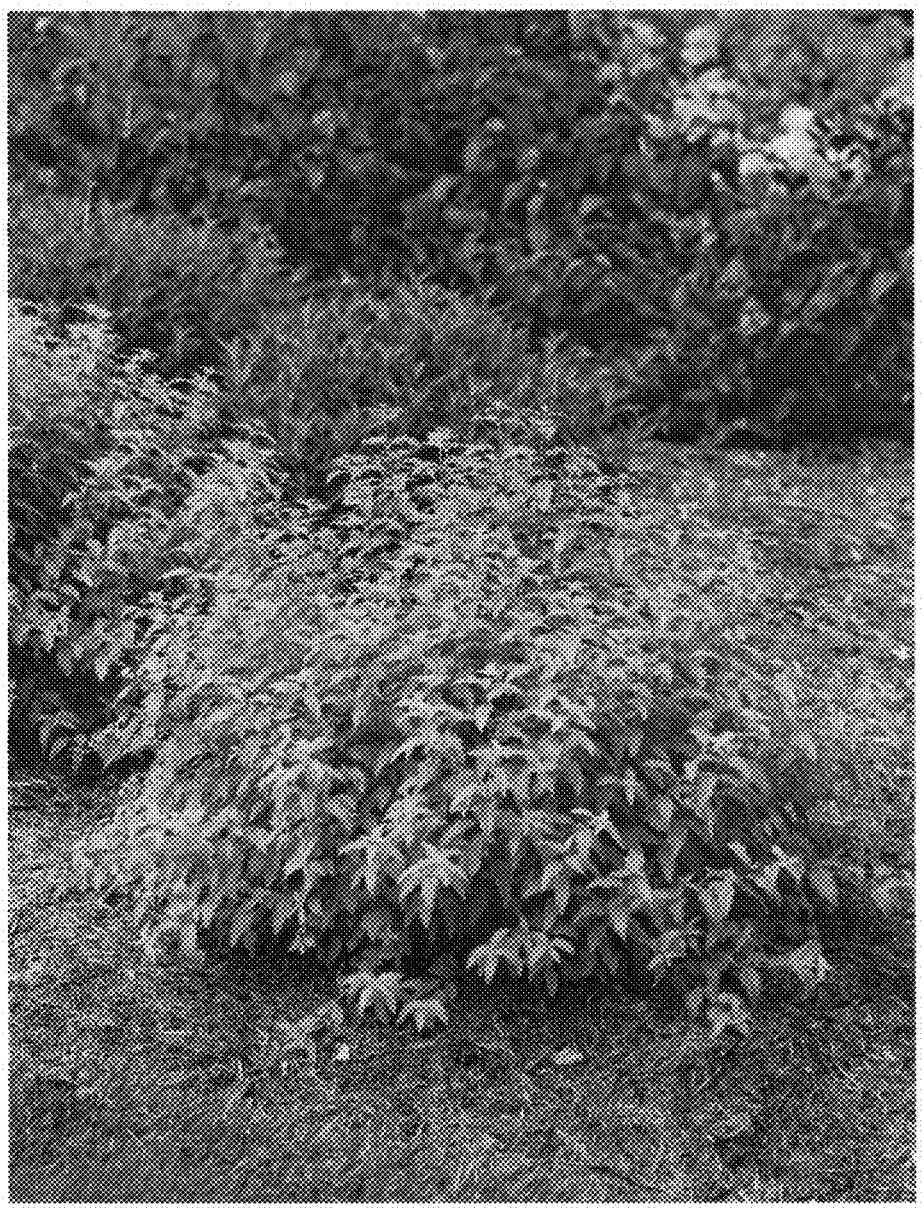
Figure 2:
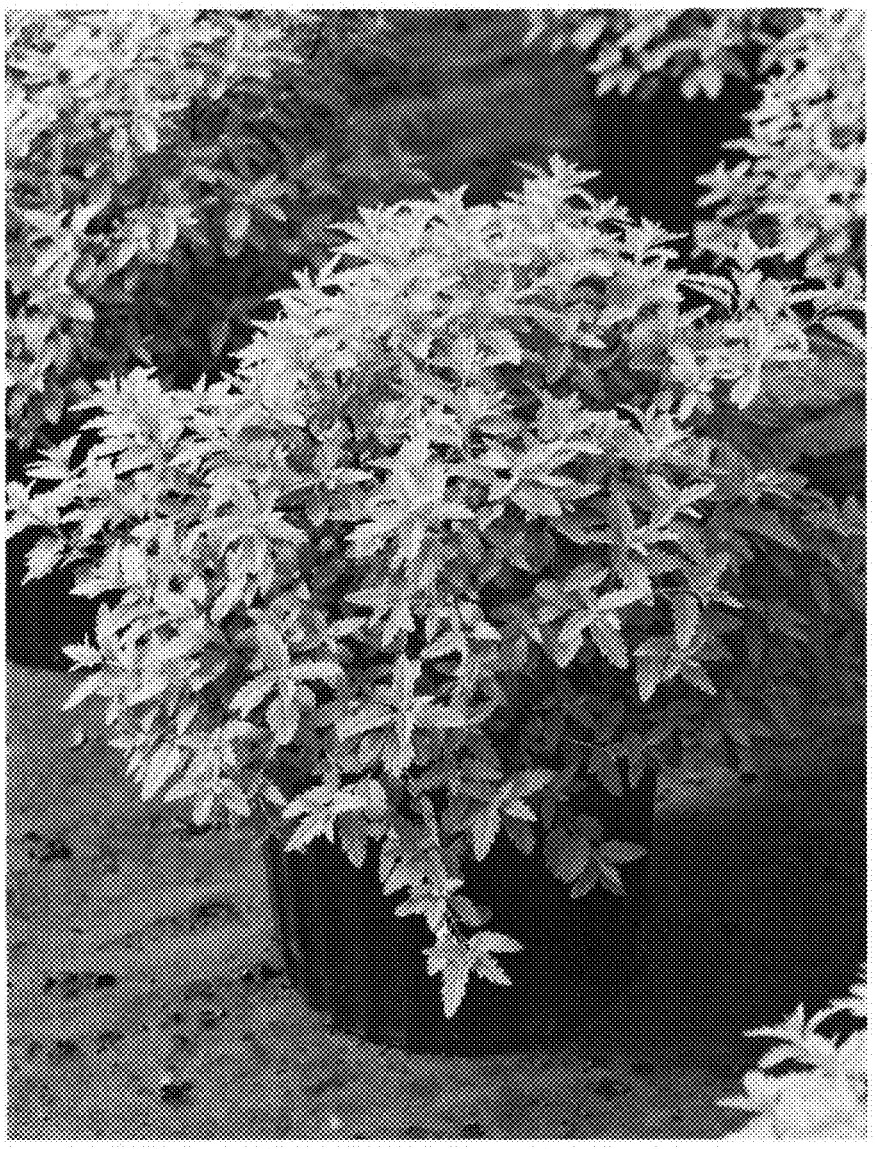
FIG. 2 illustrates a plant of approximately 1 year old in a 2 gallon container.
Figure 3:
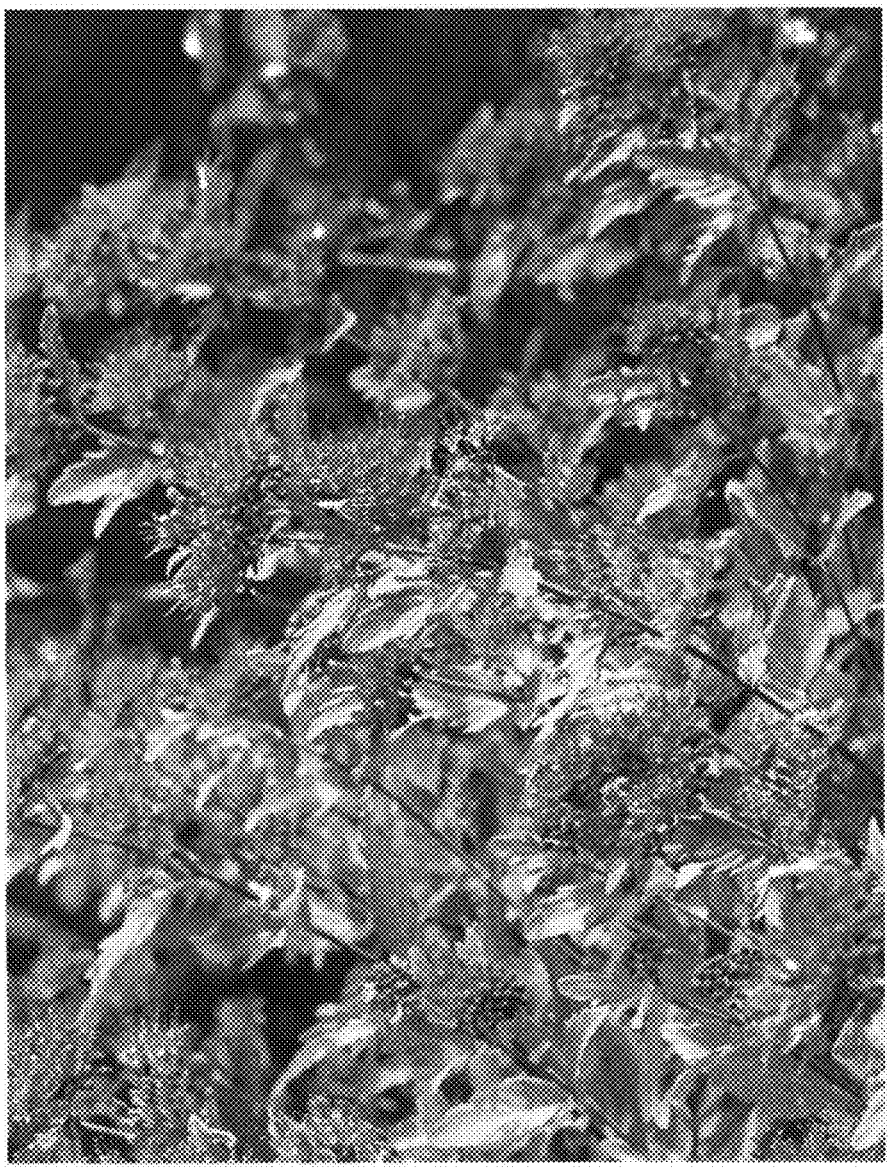
FIG. 3 illustrates a close up of the flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'SMNCVH' plants grown in a poly house during July of 2015 in Grand Haven, Mich. The growing temperature ranged from approximately 18° C. to 27° C. during the day and from approximately 5° C. to 10° C. during the night. General light conditions are normal sunlight and numerical values represent averages of typical plant types.

Botanical classification: *Caryopteris incana* 'SMNCVH'.

PROPAGATION

Type of propagation typically used: Terminal vegetative cutting.

Time to initiate roots: About 7-14 days 20° C.

Time to produce a rooted cutting: About 20-30 days at 20° C.

Root description: Fibrous, freely branching. Moderately dense, thin-medium thickness, light brown-white in color, not accurately measured with RHS Chart.

PLANT

Age of plant described: 2-3 years old from rooted cutting.

Container size: 3 gallon container.

Overall plant shape: Upright/round.

Growth habit: Upright/spreading.

Plant spread: 60-75 cm.

Plant height: 60-75 cm.

Growth rate: Moderate.

Plant vigor: Good.

Branching habit: Upright/spreading; basal branching pinching required.

Length of primary lateral branches: 30-35 cm.

Diameter of lateral branches: 6-12 mm.

Quantity of lateral branches: Approximately 25-40 branches.

Stem:

- *Color*.—New Growth: Near RHS Yellow-green 145A and Greyed-orange 176B. Mature Growth: Near RHS Grey-brown 199B.
- *Shape*.—Round.
- *Strength*.—Strong.
- *Angle of attachment*.—Approximately 45°.
- *Texture*.—Very little pubescent on new growth. Mature stem is woody.

Internode length: Average 2 cm.

FOLIAGE

Leaf:

- *Arrangement*.—Opposite, single.
- *Quantity*.—Approximately 25 to 40 per main branch.
- *Average length*.—New growth: About 2 cm Old Growth: about 3.5 cm.
- *Average width*.—New growth: about 1 cm Old Growth: about 2 cm.
- *Shape of blade*.—Ovate.
- *Apex*.—Acute.
- *Base*.—Cuneate.
- *Attachment*.—Sessile.
- *Margin*.—Lobed with pointed lobe tips.
- *Texture of top surface*.—Smooth.
- *Texture of bottom surface*.—Soft velvety texture with prominent leaf venation.
- *Other*.—Very small pubescence on the underside of the leaf with velvety texture.
- *Color*.—Young foliage upper side: Near RHS Yellow-green 145A. Young foliage under side: Near RHS Yellow-green 145C. Mature foliage upper side: Near RHS Yellow-green 144A. Mature foliage under side: Near RHS Yellow-green 146C.
- *Venation*.—Type: Pinnate. Venation color upper side: New Growth: Near RIIS Yellow-green 145C. Mature Growth: Near RHS Yellow-green 144A. Venation color under side: New Growth: Near RHS Yellow-green 145B. Mature Growth: Near RHS Yellow-green 146C. Midrib Near RHS Yellow-green 145B.
- *Petiole*.—Average Length: ~5 mm. Diameter: ~1-1.5 mm. Color: Upper: Near RHS Yellow-green 145A. Lower: Near RHS Yellow-green 145B. Texture upper and lower: Smooth/velvety texture.

FLOWER

Natural flowering season: Spring-early Summer.

Flower arrangement: Small single flowers arranged on axillary cymes.

Inflorescence form: Cymes.

Flower longevity on plant: 3 to 4 weeks.

Flowers per lateral stem: About 200.

Inflorescence size:

- *Width*.—3.0 to 3.5 cm.
- *Height*.—1.5 to 2 cm.
- *Flowers and buds per inflorescence*.—About 40.

Peduncle:

- *Length*.—6 mm.
- *Diameter*.—1 min.
- *Texture*.—Slightly pubescent.
- *Color*.—RHS Yellow-green 144D.
- *Orientation*.—Upright, straight.
- *Strength*.—Strong.

Individual flowers:

- *Type*.—Rotate.
- *Shape*.—Zygomorphic.
- *Arrangement*.—Simple.
- *Diameter*.—Approximately 0.5 cm.
- *Length*.—7 mm.
- *Aspect*.—Upright, outward facing.
- *Persistence*.—Self-cleaning.
- *Fragrance*.—None.

Petals:

- *Arrangement*.—Whorled, petals fused.
- *Appearance*.—Small; 1-2 petals contain about 8 spurs towards the tip of the petal.
- *Number*.—5 to 6.
- *Shape*.—Obovate and spurred.
- *Margin*.—Serrate.
- *Tip shape*.—Emerginate and spurred.
- *Base shape*.—Subulate.
- *Length*.—7 mm.
- *Width*.—5 to 7 mm.

*Texture*.—Upper: Smooth. Lower: Smooth.

*Color*.—When opening: Upper surface: Near RHS Violet 88D. Under surface: Near RHS Violet 88D. Fully opened: Upper surface: Near RHS Violet 88D. Under surface: Near RHS Violet 88D. Fading: Upper surface: Near RHS Violet 88D. Under surface: Near RHS Violet 88D.

Bud:

*Shape*.—Round.

*Length*.—2 mm.

*Diameter*.—2 mm.

*Color*.—Near RHS Violet-blue 91D.

Sepals:

*Appearance*.—Small; linear.

*Arrangement*.—Radial.

*Shape*.—Linear.

*Tip shape*.—Acute.

*Base shape*.—Fused.

*Margin*.—Entire.

*Quantity per flower*.—6.

*Length*.—1 mm.

*Width*.—1 mm.

*Margin*.—Entire.

*Texture*.—Upper: Smooth. Lower: Smooth, slightly pubescent.

*Color*.—Upper and lower: Near RHA Yellow-green 144D.

Calyx:

*Shape*.—Rotate, whorled.

*Length*.—3 mm.

*Diameter*.—2 mm.

Pedicel:

*Length*.—3 to 4 mm.

*Diameter*.—Less than 1 mm.

*Angle*.—Upright, outward.

*Strength*.—Moderate.

*Texture*.—Very slightly pubescent.

*Color*.—Near RHS Yellow-green 144D.

REPRODUCTIVE ORGANS

Stamens:

*Number*.—4 per flower.

*Filament length*.—8 mm.

*Filament color*.—Near RHS Violet 88C.

Anthers:

*Shape*.—Round.

*Length*.—1 mm.

*Color*.—Near RHS Violet-blue 97A.

*Pollen*.—Color: Near RHS Violet-blue 97A. Quantity: Scant.

Pistil:

*Number*.—1.

*Length*.—1 cm.

*Style*.—Length: 1 cm. Color: Near RHS Violet-blue 97D.

*Stigma*.—Shape: Acute. Color: Near RHS Violet-blue 97D. Ovary color: Near RHS Yellow-green 144B.

OTHER CHARACTERISTICS

Disease/pest resistance: Neither resistance nor susceptibility to normal diseases of *Caryopteris*. Typical pathogens include *Prodenia* and *Botrytis*. Typical pests include various Aphid and mite species.

Temperature tolerance: −31° C. lowest temperature tolerant, likely to tolerate colder. Highest temperature tolerant to 35° to 40° C.

Garden performance: Good tolerance, observed to perform well in harsh winters.

What is claimed is:

1. A new and distinct cultivar of *Caryopteris* plant named 'SMNCVH' as herein illustrated and described.

* * * * *